United States Patent
Haeusler et al.

(10) Patent No.: US 9,358,205 B2
(45) Date of Patent: Jun. 7, 2016

(54) MODIFIED STARCH DERIVATIVE-BASED MATRIX FOR COLON TARGETING

(75) Inventors: Olaf Haeusler, Fletre (FR);
Marie-Helene DeGrave, Lille (FR);
Daniel Wils, Morbecque (FR); Stefanie Krenzlin, Brandenburg (DE); Juergen Siepmann, Phalempin (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 13/880,158

(22) PCT Filed: Oct. 28, 2011

(86) PCT No.: PCT/EP2011/069060
§ 371 (c)(1),
(2), (4) Date: Apr. 18, 2013

(87) PCT Pub. No.: WO2012/056031
PCT Pub. Date: May 3, 2012

(65) Prior Publication Data
US 2013/0202691 A1   Aug. 8, 2013

(30) Foreign Application Priority Data
Oct. 29, 2010   (EP) ..................................... 10306189

(51) Int. Cl.
| A61K 9/48 | (2006.01) |
| A61K 9/00 | (2006.01) |
| A61K 9/16 | (2006.01) |
| A61K 9/20 | (2006.01) |

(52) U.S. Cl.
CPC ............. *A61K 9/0002* (2013.01); *A61K 9/1652* (2013.01); *A61K 9/205* (2013.01)

(58) Field of Classification Search
None
See application file for complete search history.

(56) References Cited

U.S. PATENT DOCUMENTS

| 6,630,586 | B1 * | 10/2003 | Fouache et al. ............... 536/103 |
| 7,431,943 | B1 * | 10/2008 | Villa .................... A61K 9/1617 424/464 |
| 2011/0097401 | A1 * | 4/2011 | Phillips ................ A61K 9/0053 424/479 |
| 2011/0256230 | A1 | 10/2011 | Haeusler et al. |

FOREIGN PATENT DOCUMENTS

| EP | 2 179 727 | 4/2010 |
| WO | 2008/132707 | 11/2008 |

OTHER PUBLICATIONS

International Search Report dated Dec. 23, 2011, corresponding to PCT/EP2011/069060.
Y. Karrout, et al; "Colon Targeting with Bacteria-Sensitive Films Adapted to the Disease State"; European Journal of Pharmaceutics and Biopharamaceutics; vol. 73, No. 1; Sep. 1, 2009; pp. 74-81.
Y. Karrout, et al; "Novel Polymeric Film Coatings for Colon Targeting: Drug Release from Coated Pellets"; European Journal of Pharmaceutical Sciences; vol. 37 No. 3-4; Jun. 28, 2009; pp. 427-433.

* cited by examiner

*Primary Examiner* — Hasan Ahmed
(74) *Attorney, Agent, or Firm* — Young & Thompson

(57) ABSTRACT

A controlled-release oral pharmaceutical composition of at least an active agent, including: a) a lipophilic matrix consisting of lipophilic compounds and/or amphiphilic compounds; and b) an hydrophilic matrix, wherein the hydrophilic matrix includes at least an indigestible polysaccharide, the active ingredient being dispersed in the lipophilic and/or the hydrophilic matrix.

The present invention also relates to a process for the preparation of such a pharmaceutical composition.

15 Claims, 7 Drawing Sheets

MODIFIED STARCH DERIVATIVE-BASED MATRIX FOR COLON TARGETING

FIELD OF THE INVENTION

The present invention relates to a new indigestible polysaccharide containing matrix for a controlled release of an active principle. The present invention also relates to the use and method for making the same.

BACKGROUND OF THE INVENTION

The local treatment of Inflammatory Bowel Diseases (e.g., Crohn's Disease and Ulcerative Colitis) is highly challenging, because conventional dosage forms rapidly release the drug in the upper gastro intestinal tract (GIT). Upon absorption into the blood stream the drug is distributed throughout the human body, resulting in potentially severe side effects. In addition, the drug concentration at the site of action—the inflamed colon—is low, leading to low therapeutic efficacies. To overcome these restrictions, drug release from the dosage form should ideally be suppressed in the stomach and small intestine, but set on as soon as the target site is reached.

Different interesting approaches have been described in the literature to allow for site specific drug delivery to the colon upon oral administration. Generally, a drug reservoir is surrounded by a film coating, which is poorly permeable for the drug in the upper GIT, but becomes permeable as soon as the colon is reached. The change in drug permeability of the film coating might be caused by: (i) the change in the pH of the contents of the GIT (stomach—small intestine—colon), (ii) degradation of the film coating by enzymes, which are secreted by colonic bacteria, or (iii) structural changes in the film coating as soon as the target site is reached (e.g., rupturing after a certain lag time, due to a steadily increasing hydrostatic pressure within the dosage form). Furthermore, drug release might start right after oral administration at a rate which is sufficiently small in order to assure that drug is still present in the dosage form once the colon is reached.

However, great care must be taken, because the conditions in the GIT of a patient suffering from Crohn's Disease or Ulcerative Colitis might significantly differ from those in a healthy subject. In particular, the pH values and transit times within the various GIT segments as well as the quality and quantity of the colonic microflora can be very different from those under physiological conditions. Thus, a dosage form which might reliably deliver a drug specifically to the colon in a healthy subject might fail in a patient. Also, the intra- and inter-variability of the dosage form's performance can be expected to be considerable if the onset of drug release is not induced in the disease state. Recently, an Indigestible polysaccharide (IPS), more particularly a branched polysaccharide containing film coatings has been proposed for colon targeting in Inflammatory Bowel Disease patients. This branched polysaccharide is a water-soluble, indigestible polysaccharide with high fiber contents, obtained from wheat starch. Importantly, it serves as a substrate for enzymes secreted from colonic bacteria present in the feces of patients suffering from Crohn's Disease and Ulcerative Colitis. However, so far, only IPS-based film coatings have been described. In these cases, a drug containing reservoir is surrounded by a continuous film, which avoids premature drug release into the contents of the stomach and small intestine.

Yet, the potential of matrix systems containing an indigestible polysaccharide as colon targeting compound is unknown. The concept of matrix systems is fundamentally different from that of film coated dosage forms. There is no "reservoir—membrane" structure. The drug is more or less homogeneously distributed throughout the dosage form. This type of devices can also be called "monolithic systems" or "one-block-systems". There is no complete local separation of the drug depot on the one hand side and the release rate controlling film coating on the other hand side. In these cases, the drug is embedded within the release rate controlling material. Since IPS as well as the most frequently used drug for the local treatment of Inflammatory Bowel Diseases [5-aminosalicylic acid (5-ASA)] are water soluble at 37° C., an additional, water-insoluble excipient is needed, for instance a lipid. MMX® is a technology used in the commercial product Lialda® aiming at colon specific delivery of 5-ASA. The idea is to embed the drug within a lipid matrix (carnauba wax and stearic acid) and to disperse this phase within a hydrogel consisting mainly of sodium carboxymethylcellulose and sodium starch glycolate. The drug-lipid-hydrogel mixture is compressed into tablets, which are film coated with Eudragit® S and Eudragit® L. Thus, this system requires a coating step and it is a single unit dosage form, suffering from the all-or-nothing effect and an eventually non-homogeneous distribution within the contents of the GIT.

The aim of the invention was to prepare and characterize novel, multiparticulate dosage forms (matrix pellets and mini tablets) usable uncoated or coated and containing the colon targeting compound IPS and high doses of an active agent such as 5-ASA. The high drug content is of major practical importance, because up to 4.8 g 5-ASA is administered per day. Different types of lipids were added to minimize premature drug release in the upper GIT and the effects of various formulation and processing parameters were studied.

The present invention also relates to a method for producing such controlled release composition.

SUMMARY OF THE INVENTION

An object of the present invention is to provide a delivery dosage form to control the rate and extent of delivery of an active ingredient, for example, without limitation an active pharmaceutical ingredient, biological, chemical, nutraceutical, agricultural or nutritional active ingredients.

Another object of the present invention is to provide a controlled-release oral pharmaceutical composition comprising a dose of an active ingredient, comprising a lipophilic matrix and a hydrophilic matrix, wherein the hydrophilic matrix comprises the indigestible polysaccharide according to the invention. The active ingredient may be at least partly inglobated in the lipophilic matrix which is then dispersed in the hydrophilic matrix when the active ingredient is hydrophobic. Inversely, when the active ingredient is hydrophilic, it may be dispersed in at least one part of the hydrophilic matrix which is then dispersed in the lipophilic matrix. The obtained granules may be subsequently dispersed in the other part of the hydrophilic matrix. Alternatively at least one active ingredient may be dispersed in each hydrophilic and lipophilic matrix prior to there mix.

The present invention provides a controlled-release oral pharmaceutical composition of at least an active agent, comprising:
  a) a lipophilic matrix consisting of lipophilic compounds and/or amphiphilic compounds;
  b) an hydrophilic matrix,
  wherein the hydrophilic matrix comprises at least an indigestible polysaccharide, the active ingredient being dispersed in the lipophilic and/or the hydrophilic matrix.

Advantageously, the indigestible polysaccharide according to a preferred embodiment is selected from a group consisting of xylooligosaccharide, inulin, oligofructose, fructo-oligosaccharide (FOS), lactulose, galactomannan, indigestible polydextrose, indigestible dextrin, trans-galacto-oligosaccharide (GOS), xylo-oligosaccharide (XOS), acemannan, lentinan, beta-glucan, polysaccharide-K (PSK), indigestible maltodextrin and partial hydrolysates thereof.

Preferably, the indigestible polysaccharide is a polysaccharide having between 15 and 50%, preferably between 20 and 40%, more preferably between 25 and 35% of 1→6 glucoside linkages, a reducing sugar content of less than 20%, preferably between 2 and 18%, more preferably between 2.5 and 15%, even more preferably between 3.5 and 10.5%, typically between 4.5 and 8%, a polymoleculiarity index of less than 5, preferably between 1 and 4%, more preferably between 1.5 and 3%, and a number-average molecular mass Mn at most equal to 4500 g/mol, more preferably between 500 and 3000 g/mol, more preferably between 700 and 2800 g/mol, more preferably between 1000 and 2600 g/mol. In a preferred embodiment, the indigestible polysaccharide is a branched maltodextrin or dextrin.

The indigestible polysaccharide according to the invention advantageously provides the controlled release effect of the pharmaceutical composition without the need of a colon targeting outer coating. The embedding matrix being a barrier to the premature releasing of the active ingredients, that is, before the colon is reached. Different physico-chemical phenomena might be involved in the control of drug release from the dosage forms described in this invention. This might potentially include for example: (i) the penetration of water into the dose form upon contact with aqueous body fluids, (ii) the dissolution of incorporated drug particles, (iii) the diffusion of dissolved drug molecules or ions through hydrophilic and lipophilic matrices, (iv) the swelling of hydrophilic compounds, (v) the dissolution of hydrophilic compounds, (v) the enzymatic degradation of system compounds, (vi) the creation of water-filled pores, through which dissolved drug molecules might diffuse.

The combination of hydrophilic matrix compounds according to the invention with lipophilic matrix compounds confers a controlled release of the active principle and optimized drug concentrations at the site of action.

The composition of the invention can further contain conventional excipients, for example bioadhesive excipients such as chitosans, polyacrylamides, natural or synthetic gums, acrylic acid polymers.

In an embodiment of the present invention, the lipophilic matrix comprises lipophilic compounds selected from unsaturated and/or hydrogenated C6-C22 alcohols or fatty acids (preferably C8-C22 fatty acids) salts, esters or amides thereof; fatty acids with glycerol or sorbitol or other polyalcohols (preferably fatty acid mono-, di- or triglycerids, polyoxyethylated derivatives thereof); waxes, ceramides, cholesterol derivatives long chain aliphatic alcohols.

In a further embodiment of the present invention, the fatty acid polyalcohol is at least one selected from the group consisting of cetostearyl alcohol, stearyl alcohol, lauryl alcohol and myristyl alcohol; fatty acid ester is at least one selected from the group consisting of glyceryl monostearate, glycerol monooleate, acetylated monoglyceride, tristearin, tripalmitin, cetyl ester wax, glyceryl palmitostearate and glyceryl behenate; and wax is at least one selected from the group consisting of beeswax, carnauba wax, glyco wax and castor wax.

Typically, the lipophilic compound is selected from soybean oil, glyceryl tristearate, glyceryl tripalmitate, glyceryl behenate, glyceryl palmitostearate, hydrogenated cottonseed oil and hydrogenated soybean oil.

In a further embodiment of the invention, the lipophilic matrix comprises amphiphilic compounds selected from polar lipids of type I or II (lecithin, phosphatidylcholine, phosphatidylethanolamine), ceramides, glycol alkyl ethers such as diethylene glycol monomethyl ether (Transcutol®), polyoxyethylenated castor oil, sodium laurylsulfate, polysorbates, phosphoacetylcholine.

Preferably, the active ingredient is embedded in the lipophilic and/or hydrophilic matrix by kneading, extrusion, granulation and/or spray drying.

Those different technologies provide an intense mixing of the ingredients.

Advantageously, the percentage of the active ingredient on the total composition weight ranges from 1 to 95%, preferably 5 to 90%, more preferably 10 to 80%, the percentage of the lipophilic matrix on the total composition weight ranges from 2.5 to 85%, preferably 15 to 80%, more preferably 20 to 70%, even more preferably 35% to 60%, the percentage of the hydrophilic matrix on the total composition weight ranges from 2.5 to 35%, preferably 10 to 30, more preferably 12 to 25%, even more preferably 15 to 20%.

The hydrophilic matrix further includes but is not limited to celluloses or their salts or derivatives thereof, hydroxyethylcellulose, hydroxypropyl cellulose, hydroxypropyl methylcellulose, sodium carboxymethyl cellulose, alginic acid or their salts and derivatives thereof, carbomer (Carbopol™), polyethyleneoxide, xanthan gum, guar gum, locust bean gum, poly vinyl acetate, polyvinyl alcohol.

According to a first embodiment, the lipophilic matrix is an inner matrix and the hydrophilic matrix is an outer matrix, the lipophilic matrix preferably forming lipophilic matrix granules containing the active ingredient.

Typically, the lipophilic matrix granules containing the active ingredient are mixed with the hydrophilic matrix in a weight ratio ranging from 100:0.5 to 100:50 (lipophilic matrix: hydrophilic matrix).

According to a second embodiment, the hydrophilic matrix is an inner matrix and the lipophilic matrix is an outer matrix, the hydrophilic matrix preferably forming hydrophilic matrix granules containing the active ingredient.

Typically, the hydrophilic matrix granules containing the active ingredient are mixed with the hydrophilic matrix in a weight ratio ranging from 100:0.5 to 100:50 (hydrophilic matrix: lipophilic matrix).

According to a third embodiment, different active ingredients may be embedded in lipophilic matrices and hydrophilic matrices and both lipophilic and hydrophilic granules may then be embedded in lipophilic and/or hydrophilic matrices.

According to a first alternative, the composition is an uncoated solid form.

This solid form is advantageously easy to be obtained. According to another advantageous alternative the composition is a coated solid form comprising an outer coating.

The outer coating may contain another active ingredient with a different releasing profile.

Typically, said outer coating is a gastro-resistant coating or colon-targeting coating.

Preferentially, the outer coating comprises hydrophobic release-modifying polymer, hydrophilic release-modifying polymer, pH-dependent release-modifying polymer or a mixture thereof, preferably methacrylic acid polymers or cellulose derivatives.

In a preferred embodiment, the outer coating is 1 to 20% by weight to total weight of the composition, and the matrix containing the drug reach 50 to 80% by weight to total weight of the composition.

The hydrophilic release-modifying polymer used for the formation of release-modifying layer, is at least one selected from the group consisting of ethylcellulose, shellac and ammonio methacrylate copolymer; said hydrophilic release-modifying polymer is at least one selected from the group consisting of hydroxyalkylcellulose and hydroxypropylalkylcellulose; and said pH-dependent release-modifying polymer is at least one selected from the group consisting of hydroxyalkylcellulose phthalate, hydroxyalkylmethylcellulose phthalate, cellulose acetyl phthalate, sodium cellulose acetate phthalate, cellulose ester phthalate, cellulose ether phthalate, and anionic copolymer of methacrylic acid with methyl or ethyl methacrylate.

According to a first variant of the invention, the composition according to the invention is in the form of granules, pellets, tablets, capsules, minitablets, wherein the active ingredient is dispersed in the lipophilic matrix and/or the hydrophilic matrix. Typically, the active ingredient is further dispersed in the outer coating.

According to a further embodiment, the active ingredient is an aminosalicylate active agent preferably chosen from 4-amino salicylic acid, 5-amino salicylic acid, and pharmaceutically acceptable salt or enantiomer or polymorph or metabolites, esters or pro-drugs thereof. The present invention also provides a process for the preparation of the compositions according to the invention, which comprises:

a) kneading or mixing a first matrix with at least an active ingredient for forming granules;

b) mixing the granules from step a) with a second matrix and optionally a subsequent step of compression and/or compaction and/or extrusion and/or spray drying;

wherein at least one of the matrices is an hydrophilic matrix and the other one is an lipophilic matrix, the lipophilic matrix containing lipophilic and/or amphiphilic compounds and the hydrophilic matrix comprising at least an indigestible polysaccharide.

Advantageously, the indigestible polysaccharide, according to a preferred embodiment, is selected from a group consisting of xylooligosaccharide, inulin, oligofructose, fructo-oligosacharide (FOS), lactulose, galactomannan and suitable hydrolysates thereof, indigestible polydextrose, indigestible dextrins and partial hydrolysates thereof, trans-galacto-oligosaccharides (GOS), xylo-oligosaccharides (XOS), acemannans, lentinans or beta-glucans and partial hydrolysates thereof, polysaccharides-K (PSK), and indigestible maltodextrins and partial hydrolysates thereof.

Preferably, the indigestible polysaccharide has between 15 and 50%, preferably between 20 and 40%, more preferably between 25 and 35% of 1→6 glucoside linkages, a reducing sugar content of less than 20%, preferably between 2 and 18%, more preferably between 2.5 and 15%, more preferably between 3.5 and 10.5%, typically between 4.5 and 8%, a polymolecularity index of less than 5, preferably between 1 and 4%, more preferably between 1.5 and 3%, and a number-average molecular mass Mn at most equal to 4500 g/mol, more preferably between 500 and 3000 g/mol, more preferably between 700 and 2800 g/mol, more preferably between 1000 and 2600 g/mol.

According to an advantageous embodiment, the process comprises a further step of film-coating of the oral solid forms from step b).

Preferably, the step a) of kneading or mixing the active ingredient with a first matrix is carried out in the absence of solvents or water-alcoholic solvents.

In a further embodiment, the process according to the invention comprises a curing time preferably at 40 to 80° C., more preferably 50 to 60° C. This thermal after-treatment might lead to changes in the inner system structure: Lipid compounds might at least partially melt and embed more efficiently drug particles.

Preferably the step a) is an extrusion and/or a granulation.

DETAILED DESCRIPTION OF THE INVENTION

Figure 1:
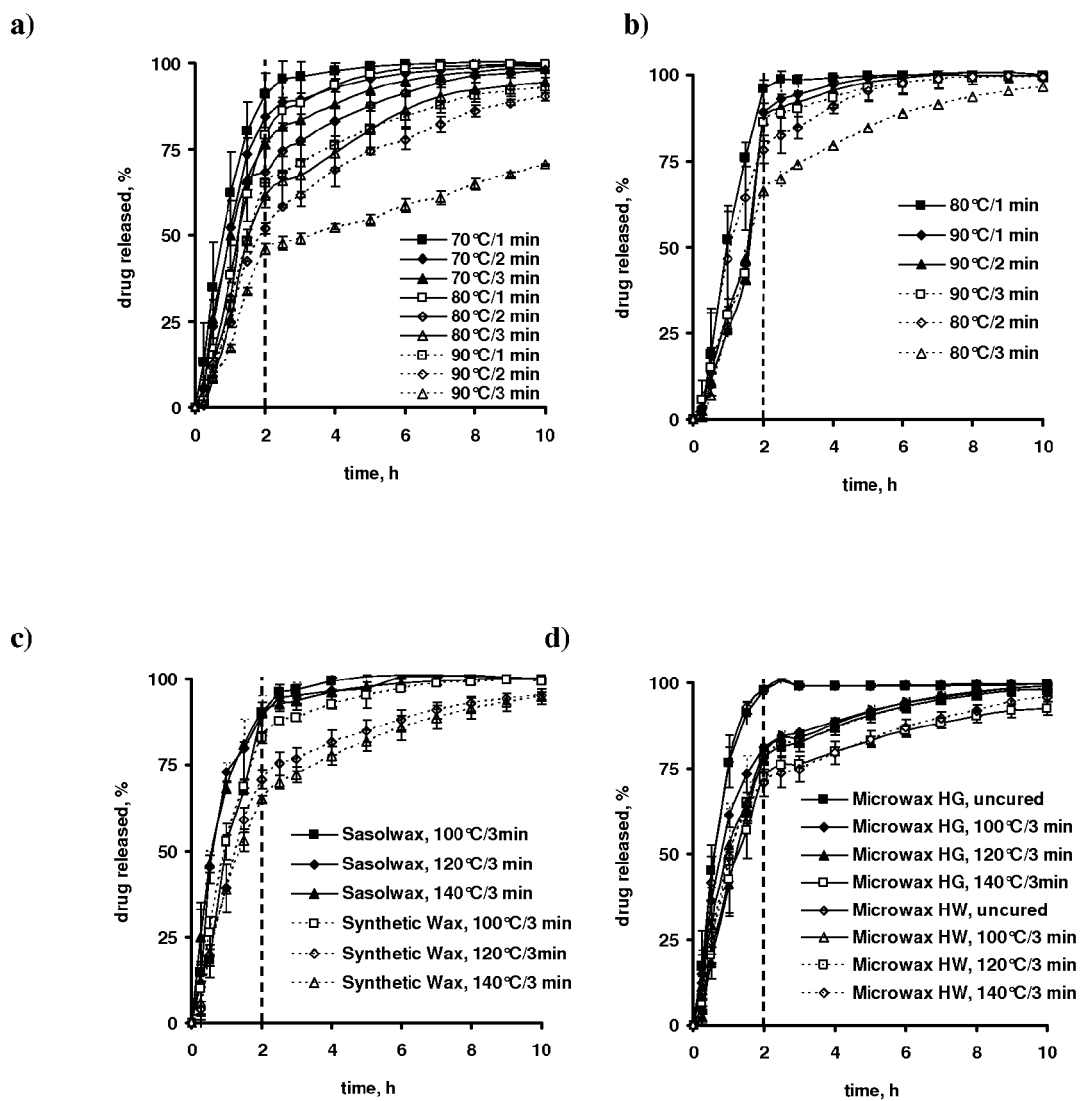
FIG. 1: 5-ASA release from pellets consisting of 60% drug, 15% IPS and 25% lipid: (a) hardened soybean oil, (b) glyceryl tristearate, (c) Sasolwax® or Synthetic Wax, or (d) Microwax® HG or Microwax® HW. The release medium was 0.1 N HCl (for the first 2 h) and phosphate buffer pH 6.8 (for the subsequent 8 h). The curing conditions are indicated in the diagrams.

In describing and claiming the present invention, the following terminology is used in accordance with the definitions set out herein.

As used herein, the term "active ingredient", "drug" or "pharmacologically active ingredient" or any other similar term means any chemical or biological material or compound suitable for administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may be systemic.

As used herein, the term "controlled release delivery" or "controlled release" means that the release of the active ingredient out of the dosage form is controlled with respect to time or with respect to the site of delivery.

The term "coat" is used herein to encompass coatings for solid supports and also capsules enclosing fluids and/or solids and the term "coated" is used similarly.

The expression "water insoluble polymer" should be understood broadly, this expression refers to polymers that do not completely dissolve in water, such as for example ethyl cellulose, certain starch derivatives or acrylic acid/methacrylic acid derivatives.

The term "indigestible polysaccharide" as used in the present invention refers to saccharides which are not or only partially digested in the intestine by the action of acids or digestive enzymes present in the human upper digestive tract (small intestine and stomach) but which are at least partially fermented by the human intestinal flora. Indigestible polysaccharide that may be employed in preferred embodiments of the invention are polysaccharides containing indigestible glucosidic linkages conferring on those saccharides additional properties identical to dietetic fibers such as "branched polysaccharides". In the sense of the invention, by branched maltodextrins or dextrins is meant maltodextrins or dextrins, of which the content of glucosidic linkages 1→6 is greater than that of standard maltodextrins or dextrins. For example, standard maltodextrins are defined as purified and concentrated mixtures of glucose and glucose polymers essentially linked in 1→4 with only 4 to 5% glucosidic linkages 1→6, of extremely varied molecular weights, completely soluble in water and with low reducing power. Examples of those indigestible polysaccharides are polydextrose, branched dextrins or branched maltodextrins such as those described in patent EP 1 006 128, of which the applicant company is the proprietor.

In practice, the number average molecular mass (Mn) and the weight average molecular mass (Mw) values which allow a better definition of the polymolecular species of the polymer mixtures, are measured by gel permeation chromatography, on chromatography columns calibrated with dextrans of known molecular weight (Alsop et al., Process Biochem, 12, 15-22; 1977 or Alsop et al., Chromatography 246, 227-240; 1982). This method of measurement is very suitable for glucose polymers and is the method used within the context of the present invention. The index of polymolecularity (I.P.) that is the ratio Mw/Mn makes it possible to characterize overall the distribution of the molecular weights of a polymer mixture.

The indigestible polysaccharide according to the present invention have a total fiber content of greater than or equal to 50% on a dry basis, determined according to AOAC method No. 2001-03 (2001).

The invention provides novel polymeric film coatings for colon targeting which are adapted to the disease state of the patients suffering from inflammatory bowel diseases. In the following, the invention will be illustrated by means of the following examples as well as the figures.

EXAMPLE

A. Materials and Methods

A.1. Materials

Aminosalicylic acid (5-ASA; Falk Pharma, Freiburg, Germany); glyceryl behenate (Compritol® 888 ATO) and glyceryl palmitostearate (Precirol® ATO 5) (Gattefosse®, St. Priest, France); hydrogenated soybean oil (Sterotex® HM) and hydrogenated cottonseed oil (Sterotex® NF) (Abitec, Janesville, Wis., USA); glyceryl trimyristate/glyceryl tripalmitate/glyceryl tristearate/hardened soybean oil (Dynasan® 114/116/118/120) and synthetic hard paraffines (Sasolwax® Spray 30 and Synthetic Wax) (Sasol, Witten, Germany); IPS (NUTRIOSE® FB 06; Roquette Freres, Lestrem, France); microcristalline cellulose (MCC, Avicel PH 101; FMC BioPolymer, Brussels, Belgium); poly(vinylpyrrolidone) (PVP, Povidone® K30) (Cooperation Pharmaceutique Francaise, Melun, France); chitosan (Protasan® C1 213; Novamatrix®, FMC BioPolymer, Drammen, Norway); Microwax® HG and Microwax® HW (Paramelt, Heerhugowaard, The Netherlands); pancreatin (from mammalian pancreas=mixture of amylase, protease and lipase) and pepsin (Fisher Bioblock, Illkirch, France).

|  | NUTRIOSE ® FB06 |
|---|---|
| Number average molecular mass Mn (g/mole) | 2640 |
| Number average molecular weight Mw (g/mole) | 4941 |
| Mn/Mw | 1.9 |
| 1-6 links | 29-32 |
| Reducing sugar | 3.9 |

A.2. Preparation of Matrix Pellets

5-ASA loaded matrix pellets were prepared by extrusion-spheronisation. The drug, IPS and the respective lipid(s) were blended and granulated manually with demineralized water in a mortar with a pestle. The obtained wet mass was extruded using a cylinder extruder with two counter-rotating rollers (1 mm orifice, 3 mm thickness, extrusion speed=32 rpm, GA 65 extruder; Alexanderwerk, Remscheid, Germany). The extrudates were subsequently spheronised (Caleva model 15; Caleva, Dorset, UK) for 180 s at 364 rpm. The obtained pellets were dried for 24 h in an oven at 40° C. and sieved (fraction: 0.71-1.00 mm). If indicated, the pellets were cured for specific time periods at defined temperatures in an oven.

A.3. Preparation of Mini Tablets

5-ASA, IPS and the respective lipid(s) were blended manually in a mortar with a pestle. Mini tablets were prepared by:

(i) direct compression on a Frank 81802 (Karl Frank, Birkenau, Germany), equipped with a 2 mm diameter punch set (Korsch, Berlin, Germany), or (ii) compression of granules obtained via melt granulation. If not otherwise stated, the respective compounds were heated and mixed on a water bath at 85° C. After cooling to room temperature, the obtained mass was ball milled, sieved (fraction 50-100 µm) and compressed using the same equipment as in (i).

The tablet height was 2 mm. Optionally, the tablets were cured in an oven for different time periods at various temperatures, as indicated.

A.4. Drug Release Measurements

Drug release from matrix pellets was measured in 120 mL cylindrical plastic flasks (diameter: 5.5 cm, height: 6.5 cm) containing 100 ml release medium: 0.1 N HCl (optionally containing 0.32% w/v pepsin) for 2 h and phosphate buffer pH 6.8 (USP 32) (optionally containing 1.0% w/v pancreatin) for 8 h (complete medium change after 2 h). The flasks were agitated in a horizontal shaker (37° C., 80 rpm, n=3) (GFL 3033; Gesellschaft fuer Labortechnik, Burgwedel, Germany). At pre-determined time points, 3 mL samples were withdrawn (replaced with fresh medium), filtered and analyzed UV-spectrophotometrically at $\lambda$=302.4 nm (0.1 N HCl), or $\lambda$=331.2 nm (phosphate buffer pH 6.8) (UV-1650PC; Shimadzu, Champs-sur-Marne, France). In the presence of enzymes, the samples were centrifuged at 13,000 rpm for 10 min (Universal 320 centrifuge; Hettich, Tuttlingen, Germany) and filtered (0.2 µm, PTFE) prior to UV measurements.

Drug release from mini tablets was measured using the USP 32 apparatus 3 (Bio Dis; Varian, Les Ulis, France) (37° C., 5 dpm, n=3) in 200 mL release medium: 0.1 N HCl for 2 h and phosphate buffer pH 6.8 (USP 32) for 8 h (complete medium change after 2 h). At pre-determined time points, 3 mL samples were withdrawn (replaced with fresh medium), filtered and analyzed UV-spectrophotometrically as described above.

A.5. Determination of Drug Solubility

Excess amounts of 5 aminosalicylic acid were placed in contact with 0.1 N HCl and phosphate buffer pH 6.8 at 37° C. in a horizontal shaker (80 rpm, GFL 3033). Samples were withdrawn every 12 h, filtered and analyzed for their drug content as described in section 2.4. until equilibrium was reached.

A.6. DSC Analysis

Thermograms of different types of pellets and raw materials (for reasons of comparison) were measured by differential scanning calorimetry (DSC1; STARe Software; Mettler Toledo SAS, Viroflay, France). Pellets were gently crushed in a mortar with a pestle and approximately 7 mg samples were heated in sealed aluminum pans (investigated temperature range: 20 to 90° C., heating rate: 10° C./min).

B. Results and Discussion

B.1. IPS-Containing Matrix Pellets

Extrusion-spheronisation allowed obtaining spherical pellets in all cases. The systems contained 60% 5 ASA, 15% IPS and 25% lipid(s) (optionally partially replaced by MCC or PVP). The high drug loading is of great practical importance, because 5 ASA is highly dosed (up to 4.8 g per day). The presence of IPS in the pellets aims at providing colon specific drug delivery: This polymer has been reported to be degraded by enzymes present in feces of Inflammatory Bowel Disease patients. The lipids, MCC and PVP aim at avoiding immediate drug release upon contact with aqueous body fluids (note that the drug and IPS are both water soluble at 37° C.).

FIG. 1 shows the release of 5 ASA from pellets containing 25% (w/w) of the following lipids: (a) hardened soybean oil, (b) glyceryl tristearate, (c) Sasolwax® or Synthetic Wax, or (d) Microwax® HG or Microwax® HW. The systems were cured at different temperatures for 1, 2 or 3 min (as indicated) in order to allow for a more homogeneous lipid distribution, more efficient embedding of the drug particles and eventually the (partial) transformation of a lipid into a more stable modification. The melting points of the investigated lipids (glyceryl tristearate: 70-73° C., hardened soybean oil: 67 72° C., Sasolwax®: 96 100° C., Synthetic Wax: 94 97° C., Microwax® HG: 80 86° C., Microwax® HW: 75 80° C.) were close to or well below the investigated curing temperatures. As it can be seen in FIG. 1, immediate drug release is avoided and the release rate generally decreased with increasing curing temperature and time, irrespective of the type of lipid. Thus, in principle the applied strategy is successful. However, in all cases drug release was too rapid and most of the drug was released during the observation period (corresponding to the simulated transit period through the upper GIT; note that long residence times have been assumed, simulating unfavorable conditions for the drug delivery system). Hence, premature drug release in vivo is highly likely. The fact that after complete medium change (at t=2 h), the release rate decreased in most cases can probably (at least partially) be attributed to the lower aqueous solubility of 5 ASA in phosphate buffer pH 6.8 compared to 0.1 N HCl at 37° C.: 4.4 mg/mL versus 10 mg/mL.

Figure 2:
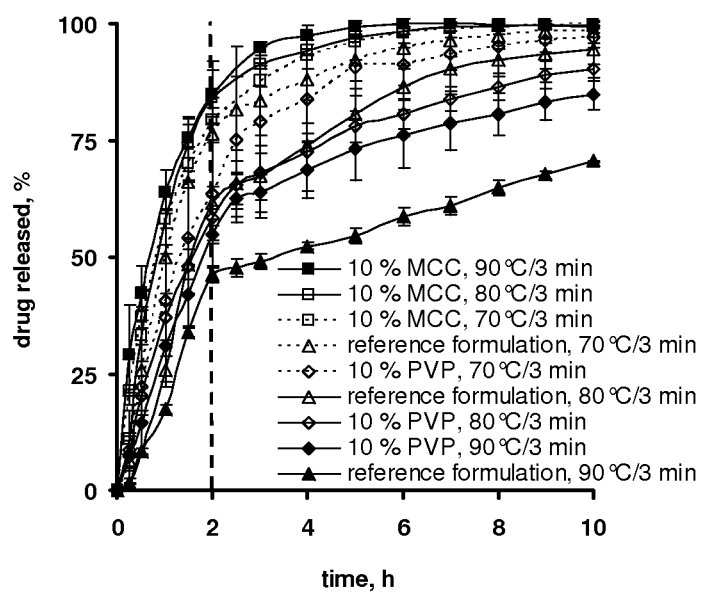
FIG. 2: Effects of the replacement of 10% hardened soybean oil by MCC or PVP (as indicated) on 5-ASA release from pellets containing 60% drug and 15% IPS. The reference formulations contained 25% hardened soybean oil. The curing conditions are indicated in the diagram, the release medium was 0.1 N HCl for 2 h, followed by phosphate buffer pH 6.8 for 8 h.

In order to reduce the undesired premature drug release in 0.1 N HCl and phosphate buffer pH 6.8, parts of the lipid were substituted by MCC or PVP. FIG. 2 shows 5-ASA release from pellets containing 60% drug, 15% IPS, 15% hardened soybean oil and 10% MCC or PVP. For reasons of comparison, also drug release from MCC/PVP-free systems (containing 25% hardened soybean oil) is shown. All pellets were cured for 3 min at 70, 80 or 90° C. (as indicated). Interestingly, the replacement of 10% (w/w, referred to the total system mass) lipid by MCC resulted in accelerated drug release, irrespective of the curing conditions. Thus, the lipid is more efficient in hindering drug release from these pellets than MCC. In contrast, the partial replacement of hardened soybean oil by PVP led to slightly/moderately decreased drug release rates, if the systems were cured at 70 and 80° C. However, upon curing at 90° C., also in this case drug release was accelerated upon lipid substitution. Thus, these approaches are not suitable to effectively minimize premature drug release in the upper GIT.

Figure 3:
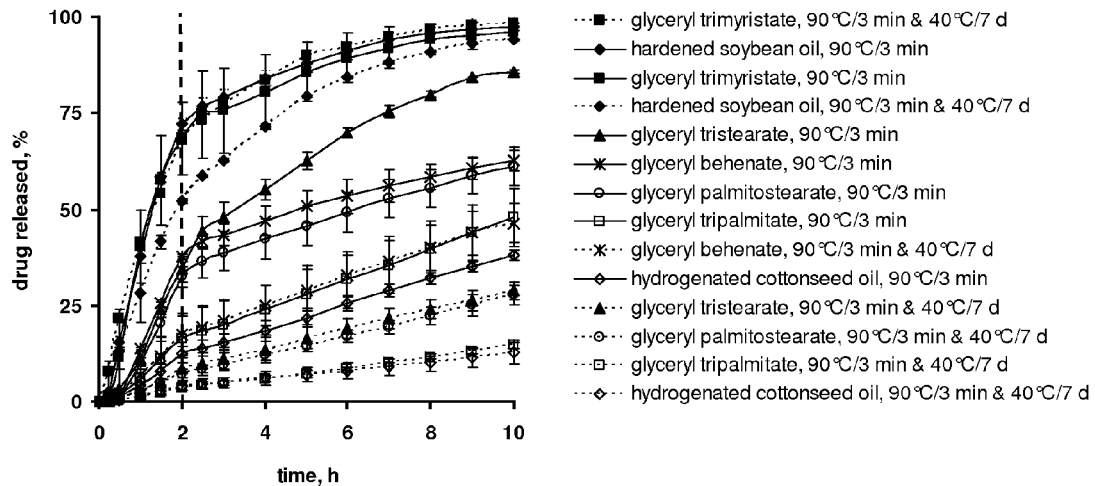
FIG. 3: Effects of an additional long term curing on drug release from pellets consisting of 60% 5-ASA, 15% IPS and 25% lipid (the type is indicated in the diagram) upon exposure to 0.1 N HCl (for 2 h) and phosphate buffer pH 6.8 (for 8 h). The solid curves indicate drug release from pellets, which were only cured for 3 min at 90° C. The dotted curves show drug release from pellets, which were additionally cured for 7 days at 40° C.
Figure 4:
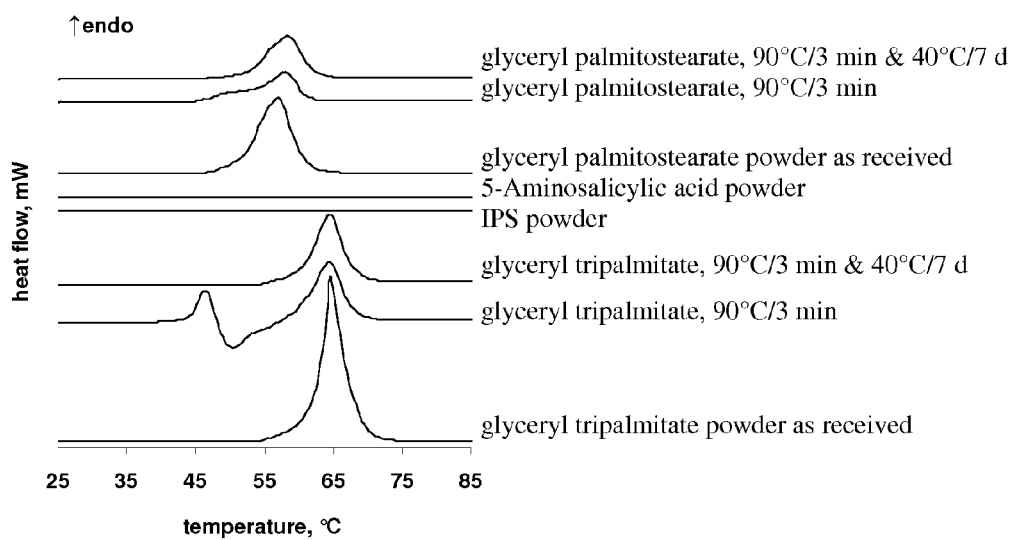
FIG. 4: DSC thermograms of pellets consisting of 60% 5-ASA, 15% IPS and 25% glyceryl palmitostearate or tripalmitate. The curing conditions are indicated in the diagram. For reasons of comparison, also thermograms of 5-ASA, IPS and the lipid powders as received are shown.

In a further attempt to avoid the observed undesired drug release in 0.1 N HCl and phosphate buffer pH 6.8, a short term curing for 3 min at 90° C. was followed by a long term curing at 40° C. for 7 days. FIG. 3 shows 5-ASA release from pellets containing 25% glyceryl trimyristate, hardened soybean oil, glyceryl behenate, glyceryl palmitostearate, glyceryl tripalmitate, hydrogenated cottonseed oil, or glyceryl tristearate upon exposure to 0.1 N HCl for 2 h, followed by phosphate buffer pH 6.8 for 8 h (dotted curves). For reasons of comparison, also drug release from pellets, which were only cured for 3 min at 90° C. are shown (solid curves). Clearly, the release rate significantly decreased in most cases upon long term curing. This can at least partially be attributed to changes in the modifications of the lipids: FIG. 4 shows exemplarily DSC thermograms of pellets consisting of 60% 5-ASA, 15% IPS and 25% glyceryl palmitostearate or tripalmitate (as indicated). The pellets were cured for 3 min at 90° C. and optionally subsequently for 7 days at 40° C. For reasons of comparison, also thermograms of 5-ASA, IPS and of the lipid powders as received are shown in FIG. 4. The melting peaks of the powders as received correspond to the melting peaks of the stable β-modifications of these lipids. In contrast, pellets which were only cured for 3 min at 90° C. also showed the melting/transformation of a less stable modification, irrespective of the type of lipid. Importantly, pellets cured for 7 days at 40° C. again only showed the melting of the stable lipid modification (in both cases). It has to be pointed out that the curing temperature during long term curing was well below the melting point of the respective lipids. Hence, the observed changes in the resulting drug release rates during long term curing are probably not caused by potential redistributions of the lipids.

Figure 5:
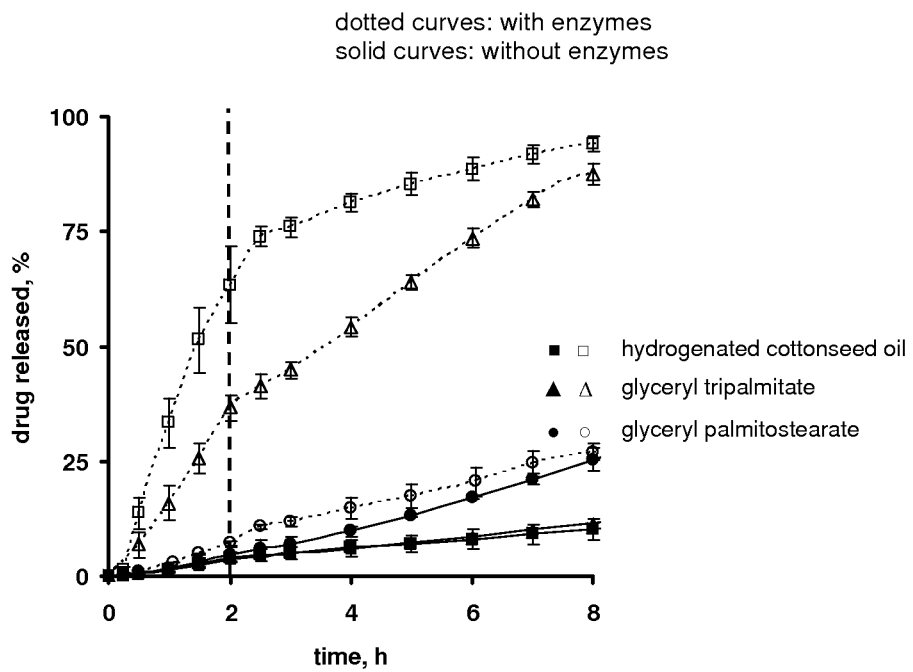
FIG. 5: Impact of the presence of enzymes in the bulk fluid [0.32% w/v pepsin in 0.1 N HCl (for 2 h), and 1% w/v pancreatin in phosphate buffer pH 6.8 (for 8 h)] on 5-ASA release from pellets consisting of 60% drug, 15% IPS and 25% lipid (the type is indicated in the diagram). All pellets were cured at 90° C. for 3 min, followed by 7 days at 40° C.

As lipids were used to slow down drug release within the upper part of the GIT, it was important to measure the effects of the presence of enzymes in the bulk fluids on drug release. FIG. 5 shows 5-ASA release from pellets consisting of 60% drug, 15% IPS and 25% hydrogenated cottonseed oil, glyceryl tripalmitate or glyceryl palmitostearate (as indicated). The release medium was either 0.1 N HCl for the first 2 h, followed by phosphate buffer pH 6.8 for the subsequent 8 h (solid curves), or 0.1 N HCl containing 0.32% w/v pepsin for the first 2 h, followed by phosphate buffer pH 6.8 containing 1% w/v pancreatin for the subsequent 8 h (dotted curves). All pellets were cured for 3 min at 90° C., followed by 7 days at 40° C. Clearly, drug release significantly increased in the presence of enzymes in the case of hydrogenated cottonseed oil and glyceryl tripalmitate, due to the (at least partial) degradation of these lipids. In contrast, the release rate only slightly increased in the case of glyceryl palmitostearate. Thus, this lipid seems to be much less affected by the added enzymes under these conditions. For this reason, glyceryl palmitostearate was used as standard lipid in all further experiments (if not otherwise stated).

Figure 6:
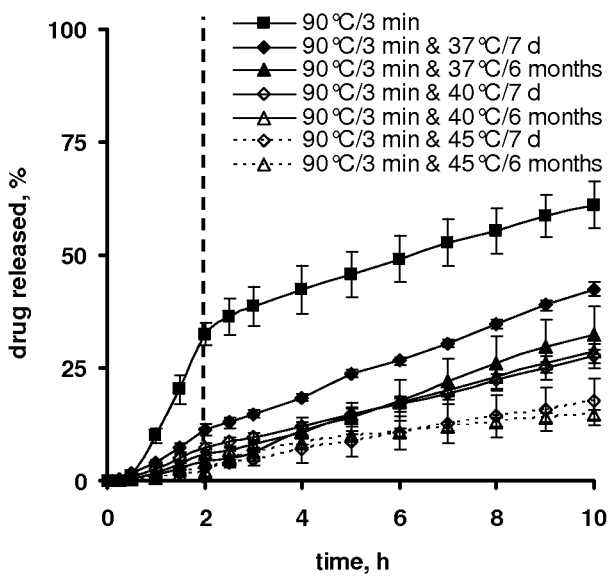
FIG. 6: Long term stability (under stress conditions) of pellets containing 60% 5-ASA, 15% IPS and 25% glyceryl palmitostearate: Drug release in 0.1 N HCl (for 2 h) and phosphate buffer pH 6.8 (for 8 h) from systems, which were cured for 3 min at 90° C., optionally followed by 7 days or 6 months at 37, 40 or 45° C. (as indicated).

When developing controlled drug delivery systems, special care needs to be taken with respect to potential changes in the systems' properties during long term storage. Modifications in the molecular structures might alter the resulting matrix permeability for the drug and, thus, the release rate. For these reasons, it is of great practical importance to measure drug release before and after long term storage from such dosage forms. Storage under stress conditions (e.g., elevated temperature) can allow obtaining results more rapidly than under ambient conditions. FIG. 6 shows the release of 5-ASA from pellets consisting of 60% drug, 15% IPS and 25% glyceryl palmitostearate. The pellets were cured for 3 min at 90° C., followed by 7 days at 37, 40 and 45° C. (as indicated) (the melting range of glyceryl palmitostearate is 53 57° C.). For reasons of comparison, also drug release from pellets, which were only cured for 3 min at 90° C. and from pellets, which were cured for 3 min at 90° C., followed by 6 months at 37, 40 and 45° C. is illustrated. Clearly, a days curing is required to slow down drug release, irrespective of the curing temperature. Interestingly, the resulting release profiles do not overlap, indicating possible differences in the lipid distribution within the system. Importantly, drug release further slowed down when increasing the curing period to 6 months in the case of curing at 37° C., but not in the case of curing at 40 or 45° C. Thus, the latter pellets are likely to be stable during long term storage at room temperature.

B.2. IPS-Containing Mini Tablets

Figure 7:
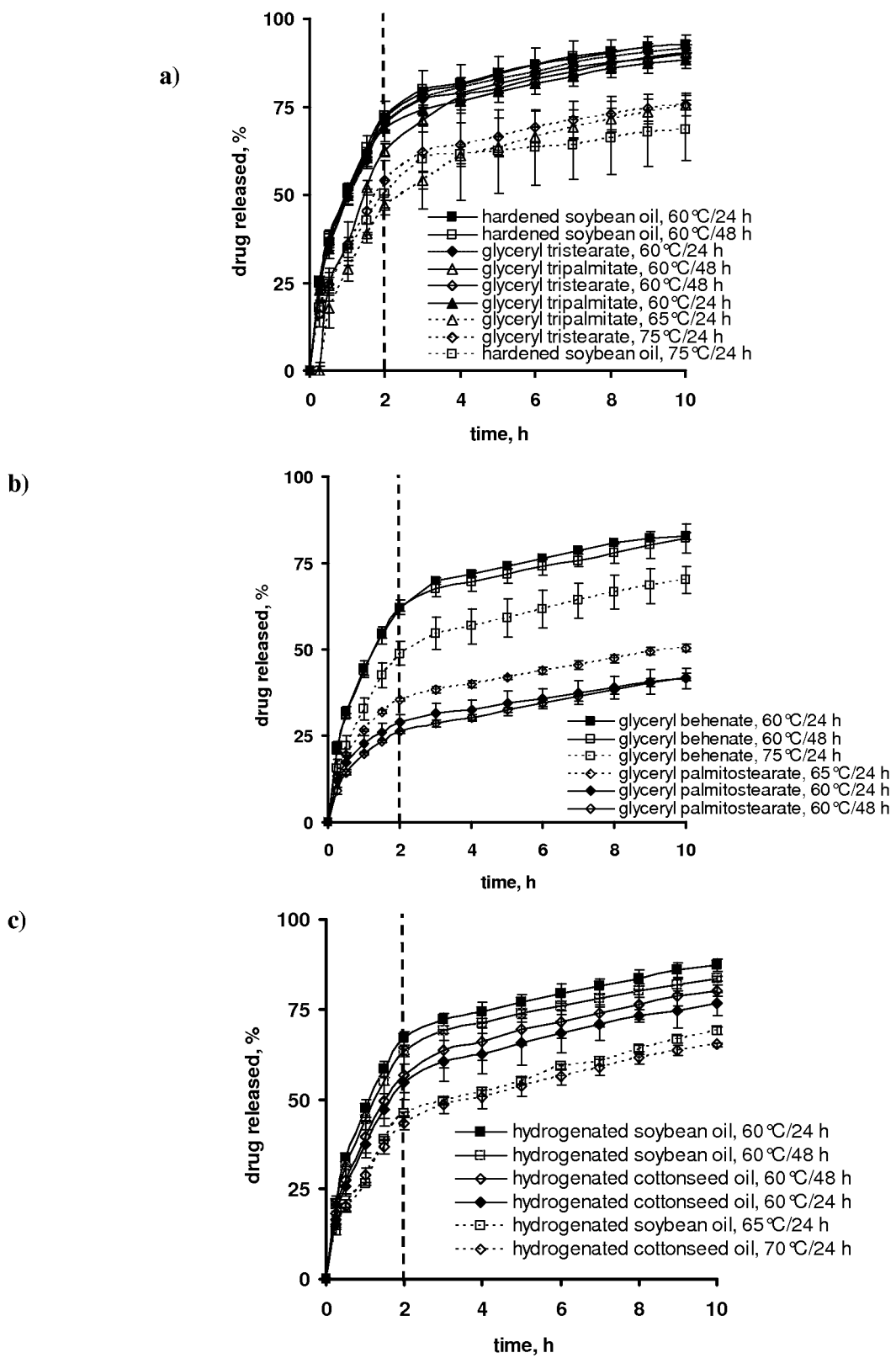
FIG. 7: 5-ASA release from mini tablets consisting of 50% drug, 15% IPS and 35% lipid: (a) glyceryl tripalmitate, glyceryl tristearate, or hardened soybean oil, (b) glyceryl behenate or glyceryl palmitostearate, (c) hydrogenated cottonseed or hydrogenated soybean oil. Drug release was measured in 0.1 N HCl for 2 h and phosphate buffer pH 6.8 for 8 h. The curing conditions are indicated in the diagrams. All tablets were prepared by direct compression.

As an alternative to matrix pellets, also mini tablets (diameter: 2 mm; height: 2 mm) consisting of 50% 5-ASA, 15% IPS and 35% lipid were prepared. Again, the high drug loading was important because of the high daily doses of 5-ASA. IPS was the colon targeting compound and the lipid was intended to minimize drug release in the upper GIT. To evaluate the suitability of different types of lipids in these dosage forms, hardened soybean oil, glyceryl tristearate, glyceryl tripalmitate, glyceryl behenate, glyceryl palmitostearate, hydrogenated cottonseed oil as well as hydrogenated soybean oil were studied (FIG. 7). The mini tablets were prepared by direct compression, followed by a curing for 24 or 48 h at 60, 65, 70 or 75° C. (as indicated), according to the melting points of the lipids: hardened soybean oil 67 72° C., glyceryl tristearate 70 73° C., glyceryl tripalmitate 63° C., glyceryl behenate 69 74° C., glyceryl palmitostearate 53 57° C., hydrogenated cottonseed oil 60 62.5° C. hydrogenated soybean oil 66.5 69.5° C. As it can be seen in FIG. 7, drug release upon 2 h exposure to 0.1 N HCl, followed by 8 h exposure to phosphate buffer pH 6.8 is considerable in all cases. Generally, the release rate decreased with increasing curing time and temperature, due to altered lipid modifications and/or lipid distribution within the system. As in the case of matrix pellets, glyceryl palmitostearate showed the most promising potential as release rate controlling lipid. For this reason it was studied in more detail.

Figure 8:
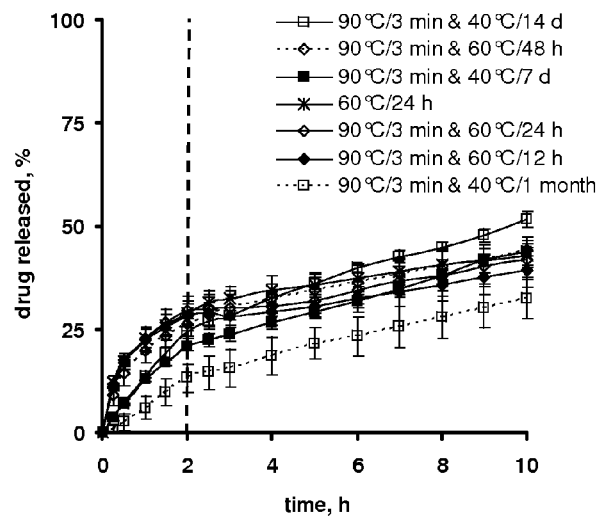
FIG. 8: Effects of the curing conditions on 5 ASA release from mini tablets consisting of 50% drug, 15% IPS and 35% glyceryl palmitostearate in 0.1 N HCl (for 2 h) and phosphate buffer pH 6.8 (for 8 h). All tablets were prepared by direct compression.
Figure 9:
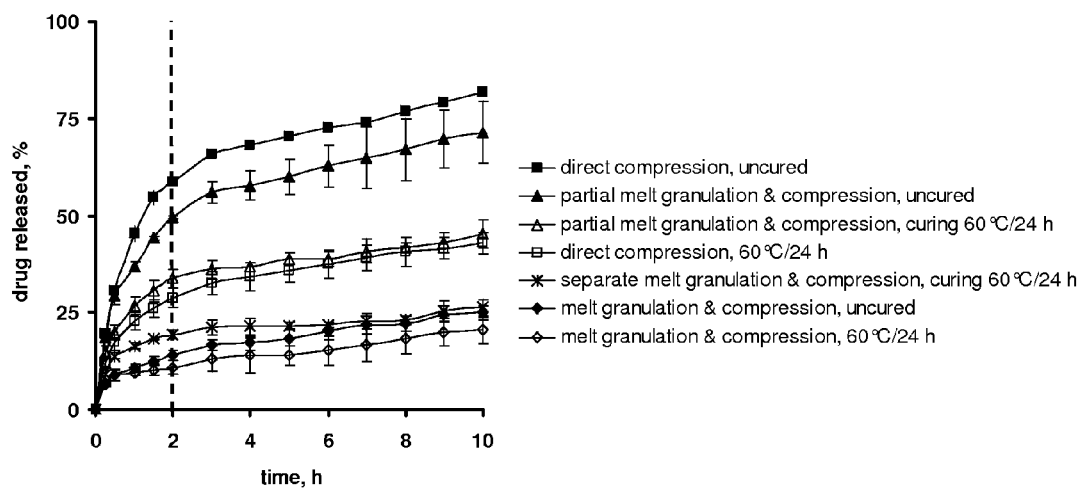
FIG. 9: Effects of the type of preparation method: direct compression versus partial melt granulation & compression versus separate melt granulation & compression versus melt granulation & compression. Details on the different preparation methods are given in the text. The mini tablets consisted of 50% drug, 15% IPS and 35% glyceryl palmitostearate. The release medium was 0.1 N HCl during the first 2 h, followed by phosphate buffer pH 6.8 during the subsequent 8 h.

In order to minimize the undesired, premature drug release in the upper GIT, the curing time and temperature were further increased. FIG. 8 shows 5-ASA release from mini tablets consisting of 50% drug, 15% IPS and 35% glyceryl palmitostearate. The systems were cured for 3 min at 90° C., followed by 7 days, 14 days or 1 month at 40° C., or by 12, 24 or 48 h at 60° C. For reasons of comparison, also 5-ASA release from mini tablets cured for 24 h at 60° C. is shown. Clearly, the release rate was not very much affected by the curing conditions, except for the 1 month curing. As the latter is difficult to realize at an industrial scale and as the release rate still remains considerable, this approach was not further investigated. Since the distribution of the lipid within the mini tablets can be expected to significantly alter its ability to hinder drug release, four different preparation techniques were studied, which are likely to result in a more or less intense embedding of the drug within the glyceryl palmitostearate: (i) direct compression, (ii) partial melt granulation & compression, (iii) separate melt granulation & compression, and (iv) melt granulation & compression. In the case of "partial melt granulation & compression", 5-ASA, IPS and 60% of the glycerol palmitostearate were molten at 85° C. on a water bath, cooled down to room temperature, ball milled and sieved (fraction 50-100 μm). The obtained powder was blended with the remaining glyceryl palmitostearate and compressed. In the case of "separate melt granulation & compression", glyceryl palmitostearate and IPS were blended in equal parts and molten at 85° C. on a water bath. The remaining glyceryl palmitostearate was blended with the drug and also this blend was molten at 85° C. on a water bath. Both melts were cooled down to room temperature, ball milled, sieved (fraction 50-100 μm), blended and compressed. In the case of "melt granulation & compression", all compounds were molten together at 85° C. on a water bath, cooled down to room temperature, ball milled, sieved (fraction 50-100 μm) and compressed. The mini tablets were optionally cured for 24 h at 60° C. As it can be seen in FIG. 9, the drug release rate decreased in the following ranking order: direct compression>partial melt granulation & compression>separate melt granulation & compression>melt granulation & compression. This was true for uncured as well as for cured mini tablets and can probably be attributed to a more and more intense embedding of the drug within the lipid.

Figure 10:
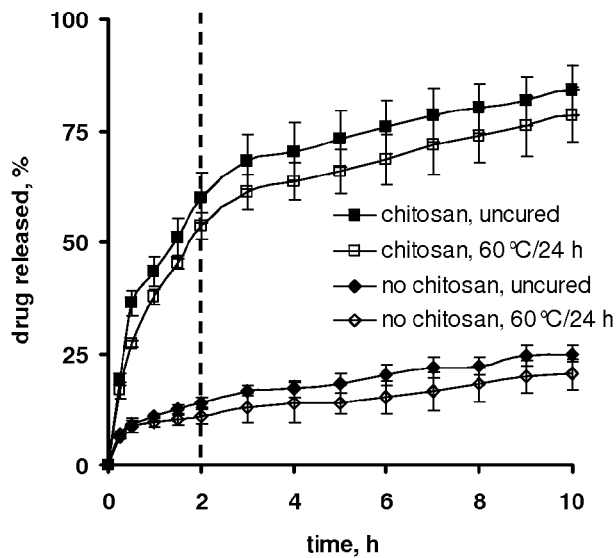
FIG. 10: Effects of the replacement of 5% glyceryl palmitostearate by chitosan on 5-ASA release from mini tablets (prepared by melt granulation & compression). The systems consisted of 50% drug, 15% IPS and 35% glyceryl palmitostearate [5% of which was replaced by chitosan, if indicated]. The release medium was 0.1 N HCl during the first 2 h, followed by phosphate buffer pH 6.8 during the subsequent 8 h.

As also chitosan has been reported to allow for site specific drug delivery to the colon, the partial substitution of glyceryl palmitostearate by chitosan was studied. FIG. 10 shows drug release from mini tablets consisting of 50% ASA, 15% IPS, 30% glyceryl palmitostearate and 5% chitosan. For reasons of comparison, also drug release from mini tablets free of chitosan (containing 35% glyceryl palmitostearate) is shown. All systems were prepared by melt granulation & compression. The tablets were either uncured or cured for 24 h at 60° C. (as indicated). Clearly, the presence of only 5% chitosan significantly increased the resulting drug release rate, leading to undesired, premature drug release. This was true for uncured as well as for cured tablets and can be attributed to the higher permeability of the hydrogel chitosan for the low molecular weight drug 5-ASA and/or rapid leaching of this compound into the surrounding bulk fluid at low pH. It has to be pointed out that an enteric coating can avoid an undesired dissolution of chitosan at low pH. Such composition is suitable for a use in a coated form.

Figure 11:
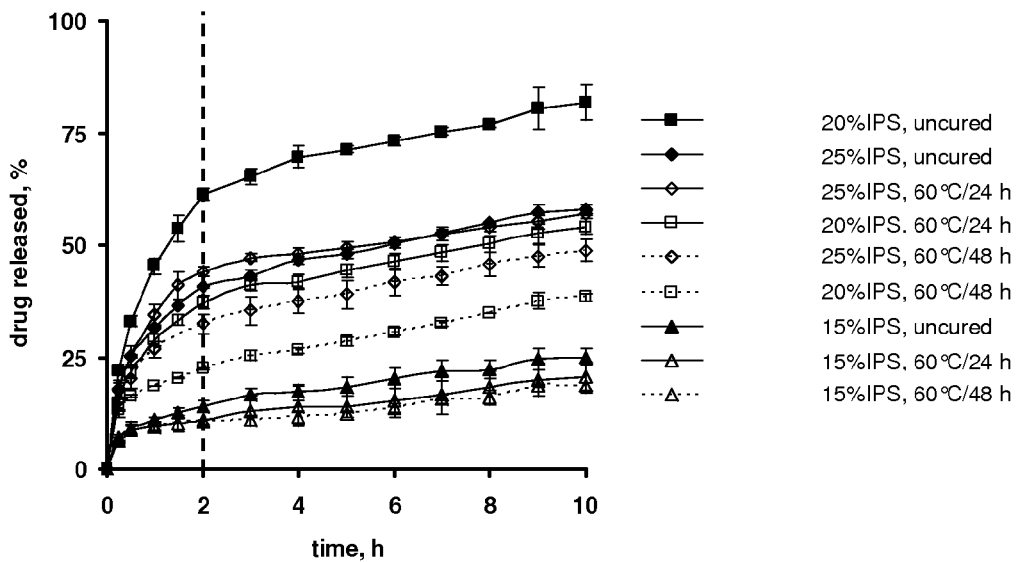
FIG. 11: Impact of the IPS content and curing conditions on 5-ASA release from mini tablets containing 50% drug and 50% "IPS+glyceryl palmitostearate" in 0.1 N HCl (for 2 h) and phosphate buffer pH 6.8 (for 8 h). The curing conditions are indicated in the diagram. All tablets were prepared by melt granulation & compression.

FIG. 11 shows the effects of the IPS content (while keeping the "IPS+glyceryl palmintostearate content" constant at 50%) and of the curing conditions on the resulting drug release kinetics from mini tablets prepared by melt granulation & compression upon exposure to 0.1 N HCl for 2 h and subsequent exposure to phosphate buffer pH 6.8 for 8 h. The IPS content was increased from 15 to 25% (while the glyceryl palmitostearate content was decreased from 35 to 25%), the tablets were optionally cured for 24 or 48 h at 60° C. (as indicated). As it can be seen, the release rate increased with increasing IPS content, because glyceryl palmitostearate is more effectively hindering drug release than IPS. Note that IPS is more effectively hindering drug release than chitosan in this type of dosage forms: When comparing 5-ASA release from mini tablets cured for 24 h at 60° C., containing 50% drug, 30% glyceryl palmitostaerate and 20% IPS (open squares and solid curves in FIG. 11) versus 15% IPS+5% chitosan (open squares in FIG. 10), it can be seen that drug release was slower in the case of 20% IPS. Furthermore, the release rate decreased with increasing curing temperature and time, irrespective of the IPS content (FIG. 11). Importantly, at a IPS level of 15%, 5-ASA release from mini tablets cured at 60° C. for 24 and 48 h is virtually overlapping (open triangles: dotted and solid curves), indicating that a stable system is likely to be achieved. Thus, mini tablets consisting of 50% 5-ASA, 15% IPS and 35% glyceryl palmitostearate prepared by melt granulation & compression and subsequent curing for 24 h at 60° C. show an interesting potential for colon specific drug delivery.

The invention claimed is:

1. An oral pharmaceutical composition of at least an active agent for controlled release in the colon of a subject suffering from an inflammatory bowel disease, comprising:
a compressed mixture of:
a lipophilic matrix consisting of lipophilic compounds and/or amphiphilic compounds,
an hydrophilic matrix comprising at least a branched maltodextrin or dextrin having between 15 and 50% of 1→6 glucoside linkages, a reducing sugar content of less than 20%, a polymolecularity index of less than 5, and a number-average molecular mass Mn at most equal to 4500 g/mol, and an active ingredient, said active ingredient being dispersed in the lipophilic matrix, the hydrophilic matrix, and throughout said compressed mixture,
wherein the compressed mixture is prepared by a process that embeds said active ingredient, at least in part, in the lipophilic matrix and is selected from the group consisting of:
(i) a direct compression process comprising blending the active ingredient, the hydrophilic matrix and lipophilic matrix to form a mixture, compressing the mixture, and curing the mixture,
(ii) a partial melt granulation and compression process comprising forming a melt granulation from the active ingredient, the hydrophilic matrix and a part of the lipophilic matrix, blending the melt granulation with a remaining part of the lipophilic matrix to form a mixture, and compressing the mixture, and, optionally, curing the compressed mixture,
(iii) a separate melt granulation and compression comprising forming a first melt granulation from the hydrophilic matrix and part of the lipophilic matrix, forming a second melt granulation from the active and a remaining part of the lipophilic matrix, blending the first melt granulation and second melt granulation to form a mixture, and compressing the mixture, and, optionally, curing the mixture, and
(iv) a melt granulation and compression process comprising forming a mixture from a melt granulation of the active ingredient, the hydrophilic matrix, and the lipophilic matrix, and compressing the mixture, and, optionally, curing the compressed mixture, and
wherein the composition is coated or uncoated, and the combination of the lipophilic matrix and the hydrophilic matrix provides a controlled release of the active ingredient into the colon of the subject.

2. The composition as claimed in claim 1, wherein the lipophilic matrix comprises lipophilic compounds selected from unsaturated and/or hydrogenated C6-C22 alcohols or fatty acids, salts, esters or amides thereof; fatty acids with glycerol or sorbitol or other polyalcohols; waxes; ceramides; cholesterol derivatives long chain aliphatic alcohols.

3. The composition as claimed in claim 1, wherein the lipophilic matrix comprises amphiphilic compounds selected from polar lipids of type I or II, ceramides, glycol alkyl ethers such as diethylene glycol monomethyl ether, polyoxyethylenated castor oil, sodium laurylsulfate, polysorbates, phosphoacetylcholine.

4. The composition as claimed in claim 1, wherein the percentage of the active ingredient on the total composition weight ranges from 1 to 95%, the percentage of the lipophilic matrix on the total composition weight ranges from 2.5 to 85%, the percentage of the hydrophilic matrix on the total composition weight ranges from 2.5 to 35%.

5. The composition as claimed in claim 1, wherein the composition is an uncoated solid form.

6. The composition as claimed in claim 1, wherein the composition is a coated solid form comprising an outer coating.

7. The composition as claimed in claim 6, wherein the outer coating comprises hydrophobic release-modifying polymer, hydrophilic release-modifying polymer, pH-dependent release-modifying polymer or a mixture thereof preferably, methacrylic acid polymers or cellulose derivatives.

8. The composition as claimed in claim 6, wherein the outer coating is 1 to 20% by weight to total weight of the composition, and the matrix containing the drug reach 50 to 80% by weight to total weight of the composition.

9. The composition as claimed in claim 1, in the form of granules, pellets, tablets, capsules, minitablets.

10. The composition as claimed in claim 9, wherein the composition is coated, and the active ingredient is also dispersed in the outer coating.

11. The composition as claimed in claim 1, wherein the active ingredient is an aminosalicylate active agent selected from the group consisting of 4-amino salicylic acid, 5-amino salicylic acid, and a pharmaceutically acceptable salt or enantiomer or polymorph or metabolites, esters or pro-drugs thereof.

12. A process for the preparation of the composition of claim 1, comprising:
  preparing a compressed mixture of the lipophilic matrix, hydrophilic matrix and the active ingredient in which the active ingredient is embedded in at least part of the lipophilic phase, by a process selected from the group consisting of:
  (v) a direct compression process comprising blending the active ingredient, the hydrophilic matrix and lipophilic matrix to form a mixture, compressing the mixture, and curing the mixture,
  (vi) a partial melt granulation and compression process comprising forming a melt granulation from the active ingredient, the hydrophilic matrix and a part of the lipophilic matrix, blending the melt granulation with a remaining part of the lipophilic matrix to form a mixture, and compressing the mixture, and, optionally, curing the compressed mixture,
  (vii) a separate melt granulation and compression comprising forming a first melt granulation from the hydrophilic matrix and part of the lipophilic matrix, forming a second melt granulation from the active and a remaining part of the lipophilic matrix, blending the first melt granulation and second melt granulation to form a mixture, and compressing the mixture, and, optionally, curing the mixture, and
  (viii) a melt granulation and compression process comprising forming a mixture from a melt granulation of the active ingredient, the hydrophilic matrix, and the lipophilic matrix, and compressing the mixture, and, optionally, curing the compressed mixture.

13. The composition as claimed in claim 7, wherein the outer coating is 1 to 20% by weight to total weight of the composition, and the matrix containing the drug reach 50 to 80% by weight to total weight of the composition.

14. The oral pharmaceutical composition according to claim 1 further comprising water.

15. An oral pharmaceutical composition of at least an active agent for treating inflammatory bowel disease, comprising:
  a compressed mixture, a compacted mixture, an extruded mixture, and/or a spray-dried mixture of:
    (a) granules comprising a first matrix and at least one active ingredient for treating inflammatory bowel disease, and
    (b) a second matrix, wherein,
  the at least one active agent is dispersed throughout the mixture,
  one of said first matrix and said second matrix is a lipophilic matrix, and one of said first matrix and said second matrix is a hydrophilic matrix,
  the lipophilic matrix consists of lipophilic compounds and/or amphiphilic compounds,
  the hydrophilic matrix comprises at least a branched maltodextrin or dextrin having between 15 and 50% of 1→6 glucoside linkages, a reducing sugar content of less than 20%, a polymolecularity index of less than 5, and a number-average molecular mass Mn at most equal to 4500 g/mol,
  the lipophilic matrix and the hydrophilic matrix, in combination, provide a controlled release of the at least one active ingredient into the colon of a subject, and
  the mixture is subjected to a process a selected from the group consisting of compression, compaction, extrusion, and a spray-drying, followed by curing to embed the at least one active ingredient, in at least part, of the lipophilic matrix.

* * * * *